United States Patent [19]

Bello

[11] Patent Number: 4,573,922

[45] Date of Patent: Mar. 4, 1986

[54] ARTIFICIAL ENDO-OSSEOUS PILLAR FOR SUPPORTING FIXED PROSTHETIC MEMBERS

[76] Inventor: Lino L. Bello, 39, Corso del Popolo, 38017 Mezzolombardo, Italy

[21] Appl. No.: 571,182

[22] Filed: Jan. 13, 1984

[30] Foreign Application Priority Data

Jan. 31, 1983 [IT] Italy ............................. 47647 A/83

[51] Int. Cl.⁴ ................................................ A61C 8/00
[52] U.S. Cl. ..................................................... 433/176
[58] Field of Search ........................................ 433/176

[56] References Cited

U.S. PATENT DOCUMENTS 2,721,387 10/1955 Ashuckian ........................... 433/176
3,465,441 9/1969 Linkow ................................ 433/176
4,225,668 9/1980 Bartoli ................................. 433/176

Primary Examiner—Robert Peshock
Attorney, Agent, or Firm—McGlew and Tuttle

[57] ABSTRACT

The invention relates to a device, metallic or of other biologically acceptable material, which is surgically inserted in the jaw bones for the purpose of artificially supporting and anchoring a fixed oral prosthetic member.

The device consists of a substantially triangular plate with a plurality of holes and notches on the surface contacting the surrounding bone. The plate has a vertical pin integrally attached to a small shoulder and serving to fix a stump that protrudes into the oral cavity and to anchor the prosthetic member in place.

9 Claims, 2 Drawing Figures

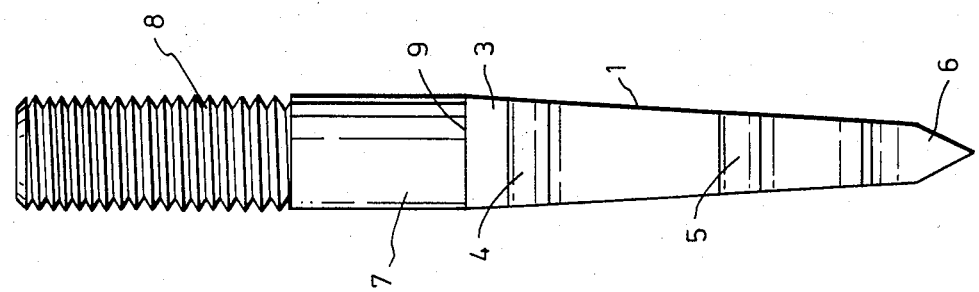
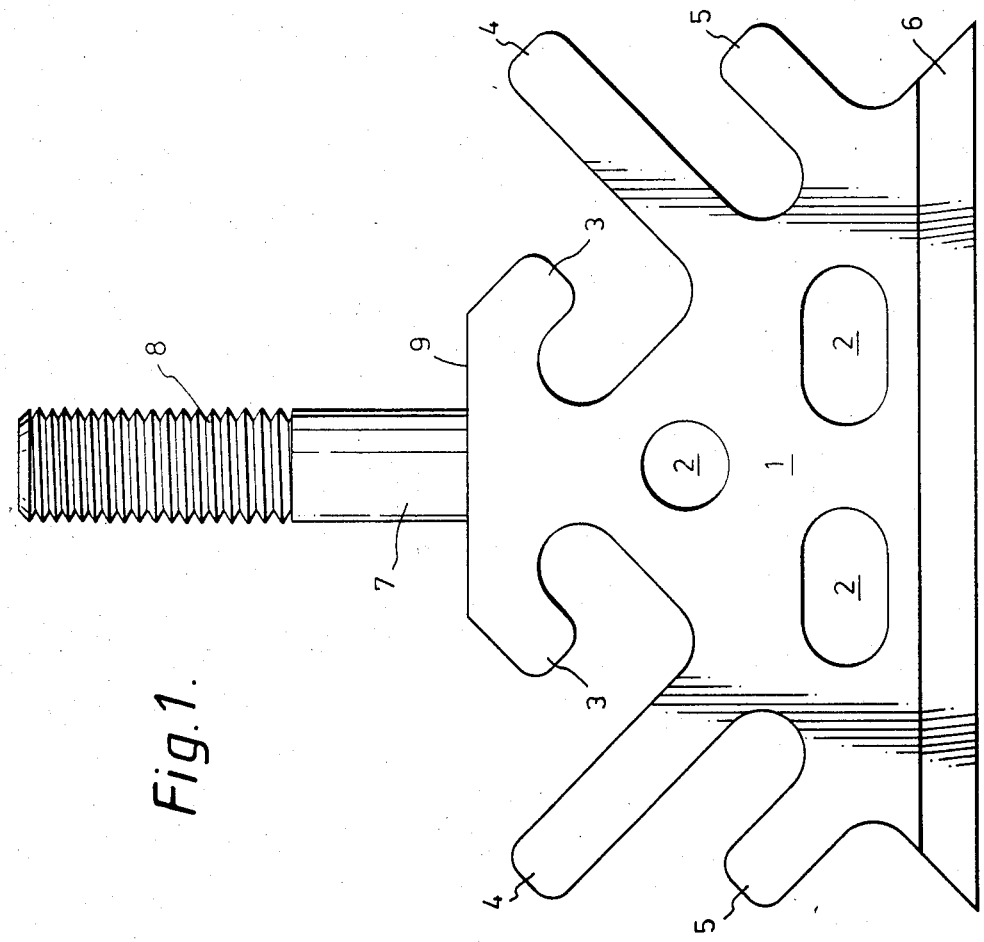

4,573,922

ARTIFICIAL ENDO-OSSEOUS PILLAR FOR SUPPORTING FIXED PROSTHETIC MEMBERS

FIELD OF THE INVENTION

The present invention relates to a device made of metal or of other biologically acceptable material, which device is surgically inserted in the upper and lower jaw bones and its purpose is to serve as an artificial pillar for anchoring and supporting a fixed prosthetic member, or a series of prosthetic members, so as to irremovably restore the chewing ability of a person, which ability had been previously reduced by the absence of teeth.

SUMMARY OF THE INVENTION

The device of the present invention essentially consists of a substantially triangular sheet or plate of metal or of other biologically acceptable material, which sheet or plate is provided with holes and notches, positioned in accordance with a predetermined pattern. The purpose is to diminish the surface which contacts the surrounding bone and to allow the bone texture to form bundles of bone fibers passing through these holes. It is thus possible to exert a holding action upon the metal sheet itself. In its upper portion, the sheet or plate is provided with a vertical pin, the free extremity of which is threaded so as to fixedly attach itself to a stump protruding into the oral cavity. The pin thusly serves the purpose of supporting the over-imposed prosthetic structure.

The structure of the device of the present invention differs from the structures of known devices in that it shows greater surface aeration. This, in turn, allow greater tolerance on the part of the adjoining bone surfaces, because the latter are less subjected to a quantitative division of the bone surface. It also permits greater nutritional possibility of the bone areas which have been divided as a result of the surgical insertion of the metal sheet or plate.

Other features and advantages of the device of the invention will become apparent from the following detailed description thereof and from the accompanying drawings, which are merely illustrative, but not limitative representations of the invention in its preferred embodiment.

THE DRAWINGS

FIG. 1 is an elevational view of the artificial endosseous pillar of the invention; and FIG. 2 is a side elevational view of FIG. 1.

DETAILED DESCRIPTION OF THE INVENTION

As shown in the accompanying drawings, the metallic (or other biologically acceptable material) sheet or plate is provided on its surface 1 with a plurality of holes 2 and along its oblique sides with projections and protrusions 3, 4, 5 of various length and configuration. These projections and protrusions are, for the most part, upwardly faced and symmetrically positioned, with respect to projections and protrusions on the opposed side of the surface 1. Such symmetry and upward facing reduces the surface contact with the surrounding bone in which the metal sheet or plate is inserted.

The base of the sheet or plate is rectilinear and the lower edge 6 is conically tapered. According to the illustrated embodiment of the invention, the device is provided in its upper portion with a vertical pin 7, the free extremity of which shows a thread 8. Thread 8 is attached or fixed to a stump (not shown) which protrudes into the oral cavity, and serves the purpose of supporting the over-imposed prosthetic structure.

Nothing, however, prevents that the anchoring of the stump on the pin 7 be carried out in a different manner, such as for example by attaching it to a cross-sectionally square or rectangular and suitably oriented pin. In any event, the base of pin 7 is integral with a shoulder 9, which is quite narrow and limited, but widens rapidly along the two oblique sides of the pin, so as to form a base which is considerably extended. This serves the purpose of insuring that good and sufficient resistance be provided against lateral pressure, that is against the lateral forces existing during the motions in and out of the dental cusps. It furthermore serves the purpose of minimizing the emergence of the shoulder, due to upper bone reabsorption, such as it is the case with other known types of devices having larger shoulders and heretofore employed.

Furthermore, the occasional emergence of an initial portion of the small shoulder, in accordance with the present invention, may be resolved surgically by simply severing in a suitable manner the minute emerged portion, without appreciably reducing the surface of the device and, thus, the adequate resistance against lateral pressures.

It is finally to be observed that, according the present invention, the vertical pressure force exerted during the chewing action or during the speaking or the swallowing actions is exerted at the vertix of the triangle, which triangle is resting on the base. This results in an improved distribution of the load and, consequently, in an appreciable reduction of the causes of sinking of the device due to a giving of the bone texture which should do the supporting. Preferably, but not necessarily, the dimensions of the present device are 15×16×2 millimeters.

What is claimed is:

1. Artificial endo-osseous pillar for supporting a fixed oral prosthetic member, which consists of a biologically acceptable plate, substantially triangularly shaped, having on its surface a plurality of holes and along the oblique sides of said surface a plurality of projections and protrusions, said projections and protrusions being of various length and upwardly faced and symmetrical to opposed ones, said plate ending at its upper extremity in a vertical pin integral with a very small shoulder, said pin serving to fix a stump that protrudes into the oral cavity, said plate ending at its lower extremity in a rectilinear and conically tapered edge.

2. The artificial pillar of claim 1, wherein said plate is made of a biologically acceptable metal.

3. The artificial pillar of claim 1, wherein said pin has a threaded free extremity.

4. The artificial pillar of claim 1, wherein said pin has a cross-sectionally free extremity so shaped as to have at least one flat and suitably oriented surface.

5. The artificial pillar of claim 1, wherein the dimensions thereof measure 15×16×2 millimeters.

6. The artificial pillar of claim 1, wherein said plate lies in a plane, all of said plurality of projections and protrusions extending in said plane and being rigid.

7. The artificial pillar of claim 6, wherein said plurality of projections includes at least one projection extending from each oblique side in a direction normal to each oblique side.

8. The artificial pillar of claim 7, wherein said plurality of projections includes one additional projection extending parallel to each oblique side and extending from said short shoulder at a location spaced from each oblique side toward a respective normal projection.

9. The artificial pillar of claim 8, wherein said plurality of holes comprises three holes extending through said plate.

* * * * *